US008029561B1

(12) United States Patent
Kopia et al.

(10) Patent No.: US 8,029,561 B1
(45) Date of Patent: Oct. 4, 2011

(54) DRUG COMBINATION USEFUL FOR PREVENTION OF RESTENOSIS

(75) Inventors: Gregory A. Kopia, Neshanic, NJ (US); Gerald H. Llanos, Stewartsville, NJ (US); Robert Falotico, Belle Mead, NJ (US)

(73) Assignees: Cordis Corporation, Miami Lakes, FL (US); Wyeth, Madison, NJ (US)

( * ) Notice: Subject to any disclaimer, the term of this patent is extended or adjusted under 35 U.S.C. 154(b) by 1826 days.

(21) Appl. No.: 09/575,480

(22) Filed: May 19, 2000

Related U.S. Application Data

(60) Provisional application No. 60/204,417, filed on May 12, 2000.

(51) Int. Cl.
*A61F 2/06* (2006.01)

(52) U.S. Cl. ..................................... 623/1.42

(58) Field of Classification Search ............... 604/95.03, 604/96.01, 101.02, 103.02, 51.53, 500, 890.1, 604/891.1; 623/11, 1.42–1.48, 1.16; 512/291, 512/56, 378, 466, 824, 521, 18, 456, 763, 512/44, 2, 93.2, 964; 424/122, 423, 424, 424/240.22
See application file for complete search history.

(56) References Cited

U.S. PATENT DOCUMENTS

| 3,657,744 A | 4/1972 | Ersek |
| 4,441,216 A | 4/1984 | Ionescu et al. ................ 3/1.5 |
| 4,503,569 A | 3/1985 | Dotter |
| 4,553,545 A | 11/1985 | Maass et al. |
| 4,580,568 A | 4/1986 | Gianturco ................ 128/345 |
| 4,733,665 A | 3/1988 | Palmaz |
| 4,800,882 A | 1/1989 | Gianturco ................ 128/343 |
| 4,856,516 A | 8/1989 | Hillstead ................ 128/343 |
| 4,886,062 A | 12/1989 | Wiktor ................ 128/343 |
| 4,907,336 A | 3/1990 | Gianturco ................ 29/515 |
| 4,969,458 A | 11/1990 | Wiktor ................ 606/194 |
| 4,990,131 A | 2/1991 | Dardik ................ 600/36 |
| 4,990,155 A | 2/1991 | Wilkoff ................ 606/191 |
| 4,994,071 A | 2/1991 | MacGregor ................ 606/194 |
| 5,015,253 A | 5/1991 | MacGregor ................ 623/1 |
| 5,035,706 A | 7/1991 | Gianturco ................ 606/198 |
| 5,041,126 A | 8/1991 | Gianturco ................ 606/195 |
| 5,064,435 A | 11/1991 | Porter ................ 623/12 |

(Continued)

FOREIGN PATENT DOCUMENTS

AU 3099900 6/2000

(Continued)

OTHER PUBLICATIONS

End, Characterization of the Antitumor Effects of the Selective Farnesyl Protein Transferase Inhibitor R115777 in Vivo and in Vitro, American Association for Cancer Research, Jan. 1, 2002, Cancer Research 61, 131-137.*

*Primary Examiner* — Patricia Bianco
*Assistant Examiner* — Camtu Nguyen

(57) ABSTRACT

The current invention comprises an approach to solving the clinical problem of restenosis, which involves the administration of combinations of drugs to patients undergoing PTCA or stent implantation. In one embodiment of the invention, an antiproliferative agent such as rapamycin, vincristine or taxol is administered in combination with the antiinflammatory agent, dexamethasone, to patients systemically, either subcutaneously or intravenously. In another embodiment of the invention, the antiproliferative and antiinflammatory agents are bound in a single formulation to the surface of a stent by means of incorporation within either a biodegradable or biostable polymeric coating. Alternatively, such drug combinations could be incorporated into a stent constructed with a grooved reservoir.

6 Claims, 5 Drawing Sheets

U.S. PATENT DOCUMENTS

| | | | | |
|---|---|---|---|---|
| 5,104,404 A | 4/1992 | Wolff | | 612/1 |
| 5,116,365 A | 5/1992 | Hillstead | | 623/1 |
| 5,122,154 A | 6/1992 | Rhodes | | 606/198 |
| 5,131,908 A | 7/1992 | Dardik et al. | | 600/36 |
| 5,133,732 A | 7/1992 | Wiktor | | 606/195 |
| 5,135,536 A | 8/1992 | Hillstead | | 606/195 |
| 5,163,958 A | 11/1992 | Pinchuk | | 623/11 |
| 5,171,262 A | 12/1992 | MacGregor | | 623/1 |
| 5,176,660 A | 1/1993 | Truckai | | 604/282 |
| 5,178,618 A | 1/1993 | Kandarpa | | 606/28 |
| 5,192,307 A | 3/1993 | Wall | | 623/1 |
| 5,217,483 A | 6/1993 | Tower | | 606/198 |
| 5,222,971 A | 6/1993 | Willard et al. | | 606/158 |
| 5,234,456 A | 8/1993 | Silvestrini | | |
| 5,246,445 A | 9/1993 | Yachia et al. | | 606/108 |
| 5,258,021 A | 11/1993 | Duran | | 623/2 |
| 5,266,073 A | 11/1993 | Wall | | 623/1 |
| 5,275,622 A | 1/1994 | Lazarus et al. | | 623/1 |
| 5,282,823 A | 2/1994 | Schwartz et al. | | 606/198 |
| 5,282,824 A | 2/1994 | Gianturco | | 606/198 |
| 5,292,331 A | 3/1994 | Boneau | | 606/198 |
| 5,304,200 A | 4/1994 | Spaulding | | 606/198 |
| 5,314,444 A | 5/1994 | Gianturco | | 606/195 |
| 5,314,472 A | 5/1994 | Fontaine | | 623/12 |
| 5,334,301 A | 8/1994 | Heinke et al. | | 204/267 |
| 5,342,348 A | 8/1994 | Kaplan | | |
| 5,342,387 A | 8/1994 | Summersq | | 606/198 |
| 5,354,257 A | 10/1994 | Roubin et al. | | 600/7 |
| 5,354,308 A | 10/1994 | Simon et al. | | 606/198 |
| 5,366,504 A | 11/1994 | Andersen et al. | | 623/11 |
| 5,370,683 A | 12/1994 | Fontaine | | 623/1 |
| 5,370,691 A | 12/1994 | Samson | | 623/12 |
| 5,375,612 A | 12/1994 | Cottenceau et al. | | 128/899 |
| 5,376,112 A | 12/1994 | Duran | | 623/2 |
| 5,382,261 A | 1/1995 | Palmaz | | 606/158 |
| 5,383,928 A | 1/1995 | Scott et al. | | |
| 5,387,235 A | 2/1995 | Chuter | | 623/1 |
| 5,389,106 A | 2/1995 | Tower | | 606/198 |
| 5,395,390 A | 3/1995 | Simon et al. | | 606/198 |
| 5,397,355 A | 3/1995 | Marin et al. | | 623/12 |
| 5,403,341 A | 4/1995 | Solar | | 606/198 |
| 5,405,377 A | 4/1995 | Cragg | | 623/1 |
| 5,411,549 A | 5/1995 | Peters | | 623/1 |
| D359,802 S | 6/1995 | Fontaine | | D24/155 |
| 5,423,885 A | 6/1995 | Williams | | 623/1 |
| 5,441,515 A | 8/1995 | Khosravi et al. | | 606/194 |
| 5,441,516 A | 8/1995 | Wang et al. | | 606/198 |
| 5,443,477 A | 8/1995 | Marin et al. | | 606/198 |
| 5,443,496 A | 8/1995 | Schwartz et al. | | 623/1 |
| 5,443,498 A | 8/1995 | Fontaine | | 623/1 |
| 5,443,500 A | 8/1995 | Sigwart | | 623/1 |
| 5,449,372 A | 9/1995 | Schmaltz et al. | | 606/198 |
| 5,449,373 A | 9/1995 | Pinchasik et al. | | |
| 5,449,382 A | 9/1995 | Dayton | | 623/1 |
| 5,464,450 A | 11/1995 | Buscemi et al. | | |
| 5,464,650 A | 11/1995 | Berg et al. | | |
| 5,500,013 A | 3/1996 | Buscemi et al. | | |
| 5,510,077 A | 4/1996 | Dinh et al. | | |
| 5,516,781 A * | 5/1996 | Morris et al. | | 514/291 |
| 5,519,042 A * | 5/1996 | Morris et al. | | 514/378 |
| 5,545,208 A | 8/1996 | Wolff et al. | | |
| 5,551,954 A | 9/1996 | Buscemi et al. | | |
| 5,554,182 A | 9/1996 | Dinh et al. | | |
| 5,562,922 A | 10/1996 | Lambert | | |
| 5,569,462 A * | 10/1996 | Martinson et al. | | 424/423 |
| 5,571,166 A | 11/1996 | Dinh et al. | | |
| 5,578,075 A | 11/1996 | Dayton | | |
| 5,591,224 A | 1/1997 | Schwartz et al. | | |
| 5,591,227 A | 1/1997 | Dinh et al. | | |
| 5,599,352 A | 2/1997 | Dinh et al. | | |
| 5,603,722 A | 2/1997 | Phan et al. | | |
| 5,605,696 A | 2/1997 | Eury et al. | | |
| 5,607,463 A | 3/1997 | Schwartz et al. | | |
| 5,607,475 A | 3/1997 | Cahalan et al. | | |
| 5,609,629 A | 3/1997 | Fearnot et al. | | |
| 5,624,411 A | 4/1997 | Tuch | | |
| 5,628,785 A | 5/1997 | Schwartz et al. | | |
| 5,629,077 A | 5/1997 | Turnlund et al. | | |
| 5,632,763 A | 5/1997 | Glastra | | 606/194 |
| 5,632,840 A | 5/1997 | Campbell | | |
| 5,637,113 A | 6/1997 | Tartaglia et al. | | |
| 5,643,312 A | 7/1997 | Fischell et al. | | 606/198 |
| 5,649,952 A | 7/1997 | Lam | | |
| 5,649,977 A | 7/1997 | Campbell | | |
| 5,651,174 A | 7/1997 | Schwartz et al. | | |
| 5,653,747 A | 8/1997 | Dereume | | 623/1 |
| 5,665,728 A * | 9/1997 | Morris et al. | | 424/122 |
| 5,669,924 A | 9/1997 | Shaknovich | | 606/108 |
| 5,672,638 A | 9/1997 | Verhoeven et al. | | |
| 5,674,242 A | 10/1997 | Phan et al. | | |
| 5,679,400 A | 10/1997 | Tuch | | |
| 5,679,659 A | 10/1997 | Verhoeven et al. | | |
| 5,693,085 A | 12/1997 | Buirge et al. | | |
| 5,697,967 A | 12/1997 | Dinh et al. | | |
| 5,697,971 A | 12/1997 | Fischell et al. | | |
| 5,700,286 A | 12/1997 | Tartaglia et al. | | |
| 5,707,385 A | 1/1998 | Williams | | |
| 5,725,567 A | 3/1998 | Wolff et al. | | |
| 5,728,420 A | 3/1998 | Keogh | | |
| 5,733,327 A | 3/1998 | Igaki et al. | | |
| 5,735,897 A | 4/1998 | Buirge | | |
| 5,755,734 A | 5/1998 | Richter et al. | | 606/194 |
| 5,755,772 A | 5/1998 | Evans et al. | | |
| 5,769,883 A | 6/1998 | Buscemi et al. | | |
| 5,776,184 A | 7/1998 | Tuch | | |
| 5,782,908 A | 7/1998 | Cahalan et al. | | |
| 5,788,979 A | 8/1998 | Alt et al. | | |
| 5,799,384 A | 9/1998 | Schwartz et al. | | |
| 5,800,507 A | 9/1998 | Schwartz | | |
| 5,800,508 A | 9/1998 | Goicoechea et al. | | 623/1 |
| 5,820,917 A | 10/1998 | Tuch | | |
| 5,820,918 A | 10/1998 | Ronan et al. | | |
| 5,824,048 A | 10/1998 | Tuch | | |
| 5,824,049 A | 10/1998 | Ragheb et al. | | |
| 5,833,651 A | 11/1998 | Donovan et al. | | |
| 5,837,008 A | 11/1998 | Berg et al. | | |
| 5,837,313 A | 11/1998 | Ding et al. | | |
| 5,843,172 A | 12/1998 | Yan | | |
| 5,849,034 A | 12/1998 | Schwartz | | |
| 5,851,217 A | 12/1998 | Wolff et al. | | |
| 5,851,231 A | 12/1998 | Wolff et al. | | |
| 5,861,027 A | 1/1999 | Trapp | | 623/1 |
| 5,865,814 A | 2/1999 | Tuch | | |
| 5,871,535 A | 2/1999 | Wolff et al. | | |
| 5,879,697 A | 3/1999 | Ding et al. | | |
| 5,882,335 A | 3/1999 | Leone et al. | | |
| 5,916,910 A * | 6/1999 | Lai | | 514/423 |
| 5,932,580 A * | 8/1999 | Levitzki et al. | | 514/249 |
| 5,981,568 A | 11/1999 | Kunz et al. | | |
| 6,159,488 A * | 12/2000 | Nagler et al. | | 424/422 |
| 6,193,746 B1 * | 2/2001 | Strecker | | 623/1.13 |
| 6,225,346 B1 * | 5/2001 | Tang et al. | | 514/445 |
| 6,284,305 B1 * | 9/2001 | Ding et al. | | 427/2.24 |
| 6,287,628 B1 * | 9/2001 | Hossainy et al. | | 427/2.24 |
| 6,299,604 B1 * | 10/2001 | Ragheb et al. | | 604/265 |
| 6,316,018 B1 * | 11/2001 | Ding et al. | | 424/423 |
| 6,335,029 B1 * | 1/2002 | Kamath et al. | | 424/423 |
| 6,369,039 B1 * | 4/2002 | Palasis et al. | | 424/93.2 |
| 6,379,382 B1 * | 4/2002 | Yang | | 623/1.13 |
| 6,387,121 B1 * | 5/2002 | Alt | | 623/1.15 |
| 6,403,635 B1 | 6/2002 | Kinsella et al. | | 206/569 |
| 6,545,097 B2 * | 4/2003 | Pinchuk et al. | | 525/240 |
| 2002/0010418 A1 * | 1/2002 | Lary et al. | | 604/101.04 |
| 2002/0061326 A1 * | 5/2002 | Li et al. | | 424/424 |
| 2002/0082680 A1 * | 6/2002 | Shanley et al. | | 623/1.16 |
| 2002/0082685 A1 * | 6/2002 | Sirhan et al. | | 623/1.42 |
| 2002/0095114 A1 * | 7/2002 | Palasis | | 604/96.01 |
| 2002/0099438 A1 * | 7/2002 | Furst | | 623/1.16 |
| 2002/0103526 A1 * | 8/2002 | Steinke | | 623/1.11 |
| 2002/0119178 A1 * | 8/2002 | Levesque et al. | | 424/423 |
| 2002/0123505 A1 * | 9/2002 | Mollison et al. | | 514/291 |
| 2002/0127327 A1 * | 9/2002 | Schwarz et al. | | 427/2.15 |
| 2002/0133222 A1 * | 9/2002 | Das | | 623/1.16 |
| 2002/0133224 A1 * | 9/2002 | Bajgar et al. | | 623/1.39 |
| 2003/0216699 A1 | 11/2003 | Falotico | | |

FOREIGN PATENT DOCUMENTS

| | | |
|---|---|---|
| DE | 3205942 A1 | 9/1983 |
| EP | 0 540 290 A2 | 10/1992 |
| EP | 0 568 310 A1 | 11/1993 |
| EP | 0734698 A2 | 3/1996 |
| EP | 0800801 A1 | 8/1996 |
| EP | 0830853 A1 | 7/1997 |
| EP | 0 950 386 | 4/1999 |
| EP | 0 540 290 A3 | 10/1999 |
| FR | 0 566 807 A1 | 4/1992 |
| GB | 1 205 743 | 9/1970 |
| GB | 0 662 307 A2 | 12/1994 |
| WO | WO96/26689 | 9/1996 |
| WO | WO 96/34580 | 11/1996 |
| WO | WO97/25000 | 7/1997 |
| WO | WO 98/19628 | 5/1998 |
| WO | WO 98/23244 A2 | 6/1998 |
| WO | WO 98 36784 A | 6/1998 |
| WO | WO 98/36784 A1 | 8/1998 |
| WO | WO 00/21584 A1 | 4/2000 |
| WO | WO 00/27445 A1 | 5/2000 |
| WO | WO 00/32255 A1 | 6/2000 |
| WO | WO 01/87376 A1 | 11/2001 |

* cited by examiner

DRUG COMBINATION USEFUL FOR PREVENTION OF RESTENOSIS

RELATED APPLICATION

This application claims benefit of a provisional application of the same title, Ser. No. 60/204,417, filed May 12, 2000.

FIELD OF THE INVENTION

This invention describes the delivery of different drug combinations, either systemically or locally, particularly from an intravascular stent, directly from micropores in the stent body or mixed or bound to a polymer coating applied on stent, to inhibit neointimal tissue proliferation and thereby prevent restenosis. This invention given either systemically or locally also facilitates the performance of the stent in inhibiting restenosis.

BACKGROUND OF THE INVENTION

Atherosclerotic lesions, which limit or obstruct coronary blood flow, are the major cause of ischemic heart disease related mortality, resulting in 500,000-600,000 deaths annually. Percutaneous transluminal coronary angioplasty (PTCA) to open the obstructed artery was performed in over 550,000 patients in the U.S. and 945,000+ patients worldwide in 1996 (Lemaitre et al., 1996). A major limitation of this technique is the problem of post-PTCA closure of the vessel, both immediately after PTCA (acute occlusion) and in the long term (restenosis): 30% of patients with subtotal lesions and 50% of patients with chronic total lesions will go on to restenosis after angioplasty. Additionally, restenosis is a significant problem in patients undergoing saphenous vein bypass graft. The mechanism of acute occlusion appears to involve several factors and may result from vascular recoil with resultant closure of the artery and/or deposition of blood platelets along the damaged length of the newly opened blood vessel followed by formation of a fibrin/red blood cell thrombus.

Restenosis after angioplasty is a more gradual process and involves initial formation of a subcritical thrombosis with release from adherent platelets of cell derived growth factors with subsequent proliferation of intimal smooth muscle cells and local infiltration of inflammatory cells contributing to vascular hyperplasia. It is important to note that multiple processes, among those including thrombosis, cell proliferation, cell migration and inflammation each seem to contribute to the restenotic process.

In the U.S., a 30-50% restenosis rate translates to 120,000-200,000 U.S. patients at risk from restenosis. If only 80% of such patients elect repeat angioplasty (with the remaining 20% electing coronary artery bypass graft) is added to the cost of coronary artery bypass graft for the remaining 20%, the total cost for restenosis easily reaches into billions of dollars. Thus, successful prevention of restenosis could result not only in significant therapeutic benefit but also in significant health care savings.

While the exact mechanism for restenosis is still uncertain, the general aspects of the restenosis process have been identified:

1) In the normal arterial wall, smooth muscle cells (SMC) proliferate at a low rate (<0.1%/day). SMC in vessel wall exists in a 'contractile' phenotype characterized by 80-90% of the cell cytoplasmic volume occupied with the contractile apparatus. Endoplasmic reticulum, Golgi, and free ribosomes are few and located in the perinuclear region. Extracellular matrix surrounds SMC and is rich in heparin-like glycosylaminoglycans which are believed to be responsible for maintaining SMC in the contractile phenotypic state (Campbell and Campbell, 1985).

2) Upon pressure expansion of an intracoronary balloon catheter during angioplasty, smooth muscle cells within the arterial wall become injured, initiating a thrombotic and inflammatory response. Cell derived growth factors such as platelet derived growth factor (PDGF), basic fibroblast growth factor (bFGF), epidermal growth factor (EGF), thrombin, etc., released from platelets (i.e., PDGF) adhering to the damaged arterial luminal surface, invading macrophages and/or leukocytes, or directly from SMC (i.e., bFGF) provoke a proliferation and migratory response in medial SMC. These cells undergo a phenotypic change from the contractile phenotype to a 'synthetic' phenotype characterized by only few contractile filament bundles but extensive rough endoplasmic reticulum, Golgi and free ribosomes. Proliferation/migration usually begins within 1-2 days post-injury and peaks at 2 days in the media, declining thereafter (Campbell and Campbell, 1987; Clowes and Schwartz, 1985).

3) Daughter synthetic cells migrate to the intimal layer of arterial smooth muscle and continue to proliferate and begin to secrete significant amounts of extracellular matrix proteins. Proliferation, migration and inflammation continue until the damaged luminal endothelial layer regenerates at which time proliferation slows within the intima, usually within 7-14 days postinjury. The further increase in intimal thickening that occurs over the next 3-6 months is due primarily to an increase in extracellular matrix rather than cell number. Thus, SMC migration and proliferation is an acute response to vessel injury while intimal hyperplasia is a more chronic response. (Liu et al., 1989).

4) Simultaneous with local proliferation and migration, inflammatory cells adhere to the site of vascular injury. Within 3-7 days post injury, luminal adherent cells decline due to migration of inflammatory to the deeper layers of the vessel wall. In animal models employing either balloon injury or stent implantation, inflammatory cells may persist at the site of vascular injury for at least 30 days (Tanaka et al., 1993; Edelman et al., 1998). Inflammatory cells therefore are present and may contribute to both the acute and chronic phases of restenosis.

Numerous agents have been examined for presumed antiproliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature, 265: 25-26, 1977; Guyton, J. R. et al., Circ. Res., 46: 625-634, 1980; Clowes, A. W. and Clowes, M. M., Lab. Invest. 52: 611-616, 1985; Clowes, A. W. and Clowes, M. M., Circ. Res. 58: 839-845, 1986; Majesky et al., Circ Res. 61: 296-300, 1987; Snow et al., Am. J. Pathol. 137: 313-330, 1990; Okada, T. et al., Neurosurgery 25: 92-98, 1989), colchicine (Currier, J. W. et al., Circulation 80: II-66, 1989, taxol (Sollott, S. J. et al., J. Clin. Invest. 95: 1869-1876, 1995), angiotensin converting enzyme (ACE) inhibitors (Powell, J. S. et al., Science, 245: 186-188, 1989), angiopeptin (Lundergan, C. F. et al., Am. J. Cardiol. 17(Suppl. B): 132B-136B, 1991), cyclosporin A (Jonasson, L. et. al., Proc. Natl., Acad. Sci., 85: 2303, 1988), goat-anti-rabbit PDGF antibody (Ferns, G. A. A., et al., Science 253: 1129-1132, 1991), terbinafine (Nemecek, G. M. et al., J. Pharmacol. Exp. Thera. 248: 1167-1174, 1989), trapidil (Liu, M. W. et al., Circulation 81: 1089-1093, 1990), tranilast (Fukuyama, J. et al., Eur. J. Pharmacol. 318: 327-332, 1996), interferon-gamma (Hansson, G. K. and Holm, J., Circulation 84: 1266-1272, 1991), rapamycin (Marx, S. O. et al., Circ. Res. 76: 412-417, 1995), steroids (Colburn, M. D. et al., J. Vasc. Surg. 15: 510-518, 1992), see also Berk, B. C. et al., J. Am. Coll. Cardiol. 17: 111B-117B 1991, ionizing radiation (Weinberger, J. et al., Int. J. Rad. Onc. Biol. Phys. 36: 767-775, 1996), fusion toxins (Farb, A. et al., Circ. Res. 80: 542-550, 1997) antisense oligonucleotides (Simons, M. et al., Nature 359: 67-70, 1992) and gene vectors (Chang, M. W. et al., J. Clin. Invest. 96: 2260-2268, 1995). Antiproliferative action on SMC in vitro has been demonstrated for many of these agents, including heparin and heparin conjugates, taxol, tranilast, colchicine, ACE inhibitors, fusion toxins, antisense oligonucleotides, rapamycin and ionizing radiation. Thus, agents with diverse mechanisms of SMC inhibition may have therapeutic utility in reducing intimal hyperplasia.

However, unlike animal models, attempts in human angioplasty patients to prevent restenosis by systemic pharmacologic means have thus far been unsuccessful. Neither aspirin-dipyridamole, ticlopidine, anticoagulant therapy (acute heparin, chronic warfarin, hirudin or hirulog), thromboxane receptor antagonist nor steroids have been effective in preventing restenosis, although platelet inhibitors have been effective in preventing acute reocclusion after angioplasty (Mak and Topol, 1997; Lang et al., 1991; Popma et al., 1991). Additionally, the 7E3 humanized monoclonal antibody fragment to the platelet GP IIb/IIIa receptor is still under study but has not shown promising results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and antiproliferative agents. These agents must be given systemically, however, and attainment of a therapeutically effective dose may not be possible; antiproliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis of dietary fish oil supplements or cholesterol lowering agents has been examined have shown either conflicting or negative results so that no pharmacological agents are as yet clinically available to prevent post-angioplasty restenosis (Mak and Topol, 1997; Franklin and Faxon, 1993; Serruys, P. W. et al., 1993). Recent 920 observations suggest that the antilipid/antioxident agent, probucol may be useful in preventing restenosis but this work requires confirmation (Tardif et al., 1997; Yokoi, et al., 1997). Probucol is presently not approved for use in the United States and a 30-day pretreatment period would preclude its use in emergency angioplasty. Additionally, application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have US Federal Regulatory Agency (FDA) approval for use for the prevention of post-angioplasty restenosis.

Unlike systemic pharmacologic therapy, stents have proven useful in partially preventing restenosis. Stents are balloon-expandable slotted metal tubes (usually, but not limited to, stainless steel), which, when expanded within the lumen of an angioplastied coronary artery, provide structural support to the arterial wall. This support is helpful in maintaining vessel lumen patency. In two randomized clinical trials, stents increased angiographic success after PTCA, by increasing minimal lumen diameter and reducing, (but not eliminating,) the incidence of restenosis at 6 months (Serruys et al., 1994; Fischman et al., 1994).

Additionally, in a preliminary trial, heparin coated stents appear to possess the same benefit of reduction in stenosis diameter at follow-up as was observed with non-heparin coated stents. Heparin coating also appears to have the added benefit of producing a reduction in sub-acute thrombosis after stent implantation (Serruys et al., 1996). Thus, 1) sustained mechanical expansion of a stenosed coronary artery with a stent has been shown to provide some measure of restenosis prevention, and 2) coating of stents with heparin has demonstrated both the feasibility and the clinical usefulness of delivering drugs locally, at the site of injured tissue.

Post-angioplasty restenosis is a multifactoral process that involves numerous interactive mechanisms. This means that effective prevention of restenosis may not be feasible with agents possessing a single mechanism of action; positive therapeutic results may be best achieved through application of several agents with differing therapeutic targets. Thus, potential therapeutic benefit could be found with the co-delivery of agents with different mechanisms of action targeting different components of the restenosis process.

SUMMARY OF THE INVENTION

The current invention comprises an approach to solving the clinical problem of restenosis, which involves the administration of drug combinations, either locally or systemically. One example of such a combination would be the addition of the antiinflammatory corticosteroid, dexamethasone, with an antiproliferative agent such as cladribine, rapamycin, vincristine, taxol, or a nitric oxide donor. Such combination therapies might result in a better therapeutic effect (less proliferation as well as less inflammation, a stimulus for proliferation) than would occur with either agent alone. Such agents could be administered systemically in their respective therapeutic doses, or, alternatively, could be bound to the surface of a stent by means of incorporation within either a biodegradable or biostable polymeric coating. Alternatively, these agents could be incorporated into a stent constructed with a grooved reservoir. Thus, delivery of a stent containing both an antiproliferative agent and an antiinflammatory agent to a coronary artery injured during the process of angioplasty would provide the added therapeutic benefit of 1) limiting the degree of local smooth muscle cell proliferation, 2) reducing a stimulus for proliferation, i.e., inflammation, and thus enhance the restenosis-limiting action of the stent.

In other embodiments of the inventions, growth factor or cytokine signal transduction inhibitor, such as the ras inhibitor, R115777, or a tyrosine kinase inhibitor, such as tyrphostin, might be combined with an antiproliferative agent such as taxol, vincristine or rapamycin so that proliferation of SMC could be inhibited by different mechanisms. Alternatively, an antiproliferative agent such as taxol, vincristine or rapamycin could be combined with an inhibitor of extracellular matrix synthesis such as halofuginone. In the above cases, agents acting by different mechanisms could act synergistically to reduce SMC proliferation and vascular hyperplasia. This invention is also intended to cover other combinations of two or more such drug agents. As mentioned above, such agents could be administered systemically, delivered locally via drug delivery catheter, or formulated for delivery from the surface of a stent, or given as a combination of systemic and local therapy.

DETAILED DESCRIPTION OF THE DRAWINGS

The invention will be better understood in connection with the following figures in which.

DETAILED DESCRIPTION OF THE INVENTION

Multiple Drug Therapy Combined with a Stent

As stated previously, implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, a combination of agents, which prevent inflammation and proliferation, or prevents proliferation by multiple mechanisms, combined with a stent may provide the most efficacious treatment for post-angioplasty restenosis. In this regard, a stent in conjunction with systemic treatment with the drug combinations suggested above or local delivery of such drug combinations is an attractive treatment. Either systemic or local delivery of multiple drugs from a stent has the following advantages:
1. Prevention of vessel recoil and remodeling through the scaffolding action of the stent;
2. Prevention of multiple components of neointimal hyperplasia, the vascular response to injury
Local administration of drug combinations to stented coronary arteries might have additional therapeutic benefit:
  1) higher tissue concentrations would be achievable than would occur with systemic administration;
  2) reduced systemic toxicity; and
  3) single treatment/ease of administration An additional benefit of combination drug therapy may be to reduce the dose of each of the therapeutic components and thus limiting their toxicity, while still achieving a reduction in restenosis. Combination therapy is therefore a means of improving the therapeutic ratio (efficacy/toxicity) of an anti-restenosis agent.

Figure 1:
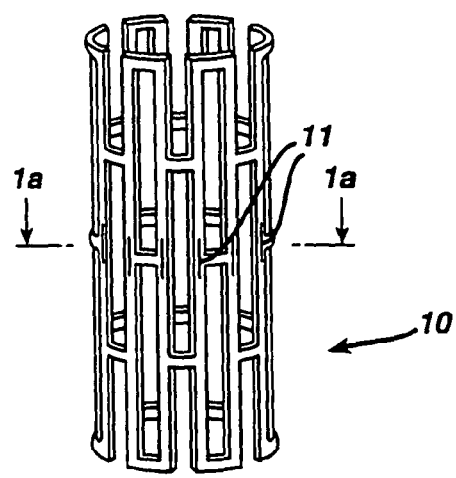
FIGS. 1 and 1a are top views and section views of a stent containing reservoirs as described in the present invention.
Figure 1A:
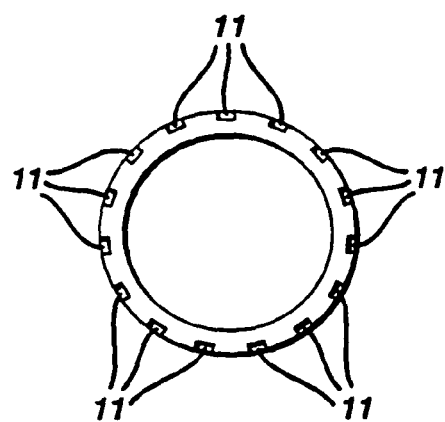
Figure 2A:
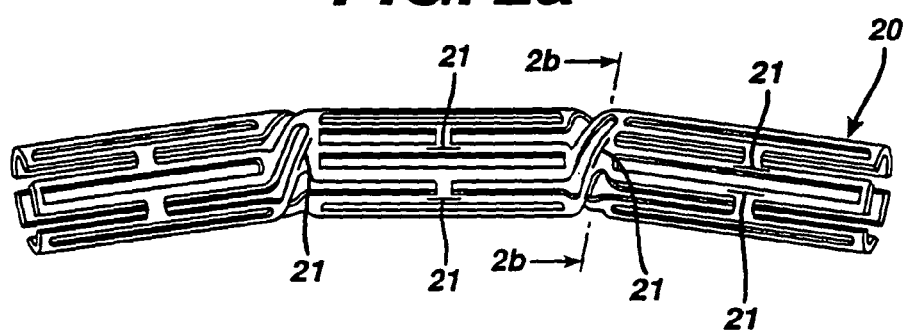
FIGS. 2a and 2b are similar views of an alternate embodiment of the stent with open ends.
Figure 2B:
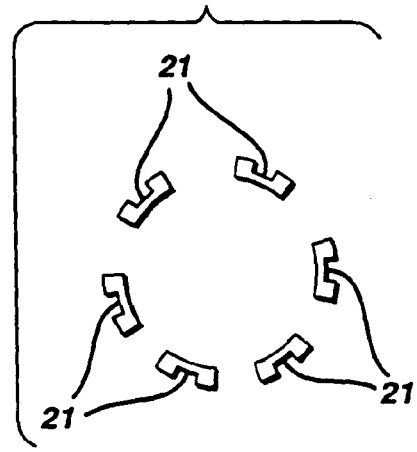
Figure 3A:
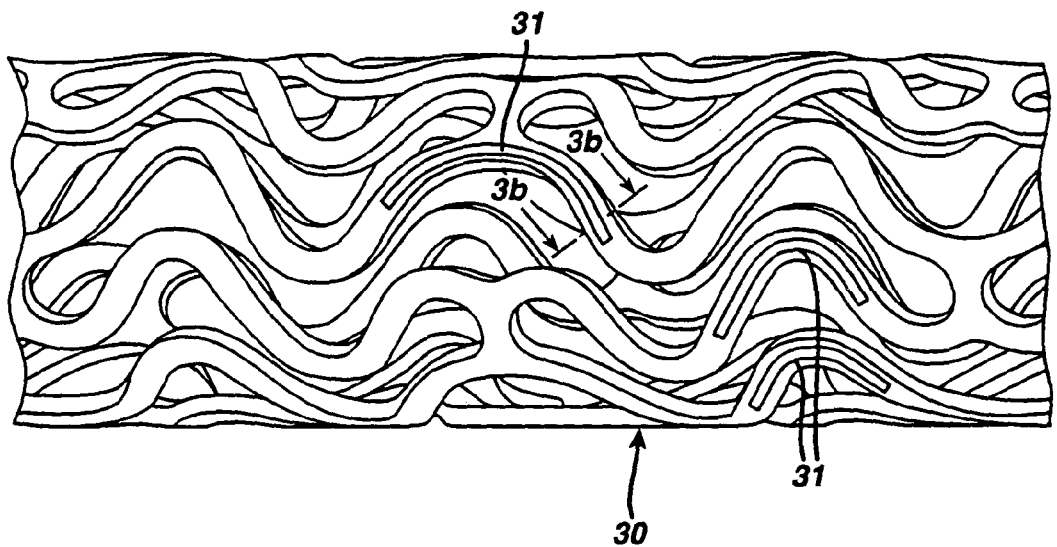
FIGS. 3a and 3b are further alternate figures of a device containing a grooved reservoir.
Figure 3B:
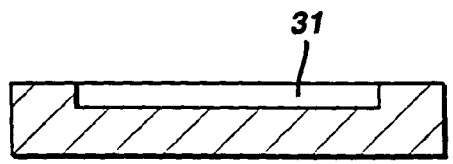
Figure 4:
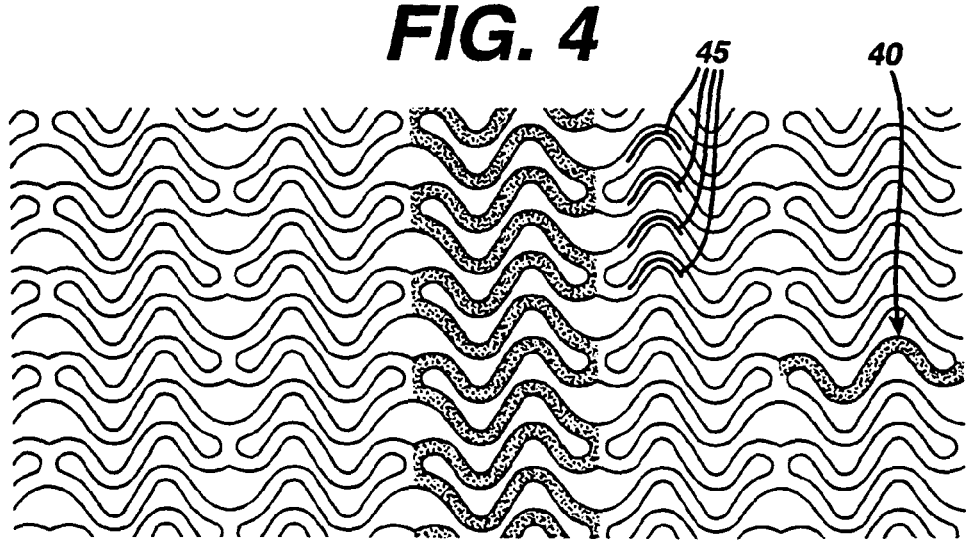
FIG. 4 is a layout view of a device containing a reservoir as in FIG. 3.

As seen in the accompanying FIGS. 1-4, it is possible to modify currently manufactured stents in order to provide adequate drug delivery. As seen in FIGS. 1a, 2a and 3a, any stent strut 10, 20, 30 can be modified to have a certain reservoir 11, 21, 31. Each of these reservoirs can be open or closed as desired. These reservoirs can hold the drug to be delivered. FIG. 4 shows a stent 40 with a reservoir 45 created at the apex of a flexible connector. Of course, this reservoir 45 is intended to be useful to deliver any drug at a specific point of flexibility of the stent. Accordingly, this concept can be useful for "second generation" type stents. Processes for coating such stents are described, for instance, in Ser. Nos. 09/061,568, filed 16 Apr. 1998, and 09/512,432 filed 25 Feb. 2000, both of which are assigned to a common assignee and are incorporated herein by reference.

In any of the foregoing devices, however, it is useful to have the drug dosage applied with enough specificity and a sufficient concentration to provide an effective dosage in the lesion area. In this regard, the reservoir size in the stent struts must be kept at a size of about 0.1 mm to about 1 mm depth, and 7 mm to 15 mm length, or enough to hold at least a therapeutic amount of the drug. Then, it should be possible to adequately apply the drug dosage at the desired location and in the desired amount. Example 1

To assess the ability of a drug combination to prevent cell proliferation, human smooth muscle cells (Clonetics, Walkersville, Md.) were seeded at a density of 10,000 cells/well) into each well of 24-well plates and cultured in growth medium containing heparin, EGF (epidermal growth factor), FGF fibroblast growth factor) and serum. After 24 hours, the growth medium was changed and fresh medium containing various concentrations of test agents (0.01-10 mcg/mL) were added to triplicate wells. Medium was replaced with fresh medium (plus test agents) after 3 days. On day five, cells were detached by trypsin/EDTA and counted using a hemacytometer. Cell viability was assessed by trypan blue exclusion.

Table 1 provides the percent of control growth of the various tested concentrations of the antiinflammatory agent, dexamethasone, on human smooth muscle cells, either in the absence or presence of 2 concentrations of the antiproliferative/antiimmune agent, rapamycin. Dexamethasone produced a concentration-related decrease in the proliferation of smooth muscle cells in this model system. The $IC_{50}$ value (concentration required to produce a reduction in proliferation to 50% of the control cell count) for the inhibition of smooth muscle cells with dexamethasone alone estimated from Table 1 is 5 µg/mL. Addition of 0.2 µg/mL of rapamycin to the incubation media was found to reduce the $IC_{50}$ estimate of dexamethasone to 0.05 µg/mL. A greater added concentration of rapamycin (2 µg/mL) further reduced the $IC_{50}$ estimate for dexamethasone to less than 0.01 µg/mL.

Thus, as the rapamycin concentration was increased in the incubation media, less dexamethasone was required to produce a 50% inhibition of cell growth. Since the amounts of rapamycin employed did not achieve a 50% inhibition of cell growth, Table 1 demonstrates that concentrations of both rapamycin or dexamethasone below their respective $IC_{50}$ amounts may combine to produce an effect on cell growth greater than either agent individually. Such a drug combination may be therapeutically useful for inhibition of the intimal smooth muscle cell proliferation that accompanies stent implantation. While efficacy could be maintained at these lower doses, toxicities associated with each of these agents might be ameliorated.

TABLE 1

Inhibition of human vascular smooth muscle cell proliferation with dexamethasone or dexamethasone + rapamycin.

| % of Control Growth | Concentration of Dexamethasone (μg/ml) | | | | | | | | | |
|---|---|---|---|---|---|---|---|---|---|---|
| | 0 | 0.01 | 0.05 | 0.1 | 0.5 | 1 | 5 | 10 | 50 | 100 |
| Rapamycin 0 ug/ml | 100.0 | — | — | 75.2 | 76.5 | 72.2 | 50.0 | 36.1 | 18.3 | 11.7 |
| Standard Deviation | 4.2 | | | 0.8 | 16.3 | 9.3 | 7.6 | 5.9 | 6.0 | 1.3 |
| Rapamycin 0.2 ug/ml | 85.7 | 63.4 | 57.6 | 49.7 | 48.9 | 48.2 | 41.2 | 31.1 | 31.2 | 29.0 |
| Standard Deviation | 6.6 | 3.2 | 2.1 | 4.6 | 2.2 | 1.7 | 3.0 | 2.7 | 1.0 | 1.8 |
| Rapamycin 1 ug/ml | 67.4 | 48.3 | 45.1 | 38.1 | 39.2 | 37.8 | 33.9 | 25.8 | 20.7 | 18.5 |
| Standard Deviation | 2.6 | 3.3 | 13.3 | 9.5 | 4.4 | 4.5 | 3.1 | 8.1 | 6.4 | 3.7 |

The following examples are used to demonstrate the various configurations of medicated stent coatings containing one or more drugs. These are summarized in Table 2.

TABLE 2

Coating configurations used to demonstrate controlled release of rapamycin and dexamethasone from a stent

| Sample I.D | Drug Content | | Coating Configuration |
|---|---|---|---|
| | Rap[a] | Dex[b] | |
| 50/50 | 82 μg | 82 μg | Drugs are co-mixed with polymer. Total coating wt.: 548 μg |
| 0/100 | 0 μg | 100 μg | Drugs are co-mixed with polymer. Total coating wt.: 641 μg |
| 100/0 | 150 μg | 0 μg | Drugs are co-mixed with polymer. Total coating wt.: 500 μg |
| 67/33 | 103 | 51 | Drugs are co-mixed with polymer. Total coating wt.: 513 μg |
| 33/67 | 53 | 107 | Drugs are co-mixed with polymer. Total coating wt.: 534 μg |
| 33/67-3X[c] | 182 μg | 363 μg | Drugs are mixed with polymer. Total coating wt.: 1817 μg |
| 50/50-OLD[d] | 77 μg | 80 μg | Base coat: Rapamycin mixed with polymer. Overcoat: Dexamethasone mixed with polymer. Total coating wt.: 520 μg |
| 50/50-OLR[e] | 79 μg | 81 μg | Base coat: Dexamethasone mixed with polymer. Overcoat: Rapamycin mixed with polymer. Total coating wt.: 536 μg |
| 50/50-TC[f] | 100 μg | 100 μg | Base coat: Drugs are mixed with polymer blend Barrier coat: 158 μg polybutyl methacrylate. Total coating wt.: 811 μg |
| 0/100-TC[f] | 0 μg | 196 μg | Base coat: Drugs are mixed with polymer blend Barrier coat: 168 μg polybutyl methacrylate. Total coating wt.: 839 μg |

[a]Rapamycin;
[b]Dexamethasone;
[c]3 time coating thickness;
[d]Dexamethasone overlayer;
[e]Rapamycin overlayer;
[f]Top coated Example 2

This example describes the preparation of a base coating that contains rapamycin Stents were coated with Parylene C™ using a vapor deposition method provided by the manufacturer of the parylene-coating instrument (SCS Madison, Wis.). The stent is weighed and then mounted for coating. While the stent is rotating a solution of 1.75 mg/ml Poly (ethylene-covinyl acetate)(PEVA), 1.75 mg/ml polybutyl methacrylate, and 1.5 mg/ml rapamycin dissolved in tetrahydrofuran is sprayed onto it. The coated stent is removed from the spray and allowed to air-dry. After a final weighing the amount of coating on the stent is determined.

Example 3

This example describes the preparation of a base coating that contains dexamethasone Stents were coated with Parylene C™ using a vapor deposition method provided by the manufacturer of the parylene-coating instrument (SCS Madison, Wis.). The stent is weighed and then mounted for coating. While the stent is rotating a solution of 1.75 mg/ml Poly (ethylene-co-vinyl acetate)(PEVA), 1.75 mg/ml polybutyl methacrylate, and 1.5 mg/ml dexamethasone dissolved in tetrahydrofuran is sprayed onto it. The coated stent is removed from the spray and allowed to air-dry. After a final weighing the amount of coating on the stent is determined.

Example 4

This example describes the preparation of a base coating that contains rapamycin and dexamethasone Stents were coated with Parylene C™ using a vapor deposition method provided by the manufacturer of the parylene-coating instrument (SCS Madison, Wis.). The stent is weighed and then mounted for coating. While the stent is rotating a solution of 1.75 mg/ml Poly (ethylene-co-vinyl acetate)(PEVA), 1.75 mg/ml polybutyl methacrylate, 0.75 mg/ml rapamycin and 0.75 mg/ml dexamethasone dissolved in tetrahydrofuran is sprayed onto it. The coated stent is removed from the spray and allowed to air-dry. After a final weighing the amount of coating on the stent is determined.

Example 5

This example describes a stent coating that consists of a base coat containing rapamycin and dexamethasone and a drug-free barrier overcoat A stent is coated as in Example 4. After the coating is thoroughly dried a solution of 2.5 mg/ml polybutyl methacrylate dissolved in tetrahydrofuran is sprayed onto it. It is then air-dried for a final overcoat weight of 150 μg.

Example 6

This example describes a stent coating, which consists of a base containing rapamycin and an overlayer with dexamethasone A stent is coated as in Example 2. A solution of 1.75 mg/ml Poly (ethylene-co-vinyl acetate)(PEVA), 1.75 mg/ml polybutyl methacrylate, and 1.5 mg/ml dexamethasone dissolved in tetrahydrofuran is sprayed onto it. The coated stent is removed from the spray and allowed to air-dry. The final weight of each layer is typically 250 µg for a total coating weight of 500 µg.

Example 7

This example describes a stent coating, which consists of a base containing dexamethasone and an overlayer with rapamycin A stent is coated as in Example 3. A solution of 1.75 mg/ml Poly (ethylene-co-vinyl acetate)(PEVA), 1.75 mg/ml polybutyl methacrylate, and 1.5 mg/ml rapamycin dissolved in tetrahydrofuran is sprayed onto it. The coated stent is removed from the spray and allowed to air-dry. The final weight of each layer is typically 250 µg for a total coating weight of 500 µg.

The following examples describe the method and results for testing the in vitro release of rapamycin and dexamethasone from coated stent.

Example 8

This example describes the method for performing the in vitro release of rapamycin and dexamethasone from coated stent.

Each stent was placed in a 2.5 mL of release medium (aqueous ethanol, 25 percent by volume at room temperature) contained in a 13×100 mm culture tube with a screw cap. The tube was shaken in a water bath (INNOVA™ 3100, New Brunswick Scientific) at 200 rpm while maintaining ambient conditions. After a given time interval (ranging from 15 minutes to one day) the tubes were removed from the shaker and the respective stents carefully transferred to a fresh 2.5 ml Aliquot of release medium. The new tube was placed on the shaker and agitation resumed. A sample was removed from the aliquot, which had previously contained the stent and placed in a HPLC vial for determination of the rapamycin content and dexamethasone, by HPLC.

Example 9

This example describes the method for analyzing the release medium for rapamycin.

The HPLC system used to analyze the samples was a Waters Alliance with a PDA 996. This system is equipped with a photodiode array detector. 20 µL of each sample was withdrawn and analyzed on a $C_{18}$-reverse phase column (Waters Symmetry™ Column: 4.6 mm×100 mm $RP_{18}$, 3.5 µm with a matching guard column) using a mobile phase consisting of acetonitrile/methanol/water (38:34:28 v/v) delivered at a flow rate of 1.2 mL/min. The column was maintained at 60° C. through the analysis. Under these analytical conditions rapamycin had a retention time of 4.75±0.1 minutes. The concentration was determined from a standard curve of concentration versus response (area-under the curve) generated from rapamycin standards in the range of from 50 ng/mL to 50 µg/mL.

Figure 5:
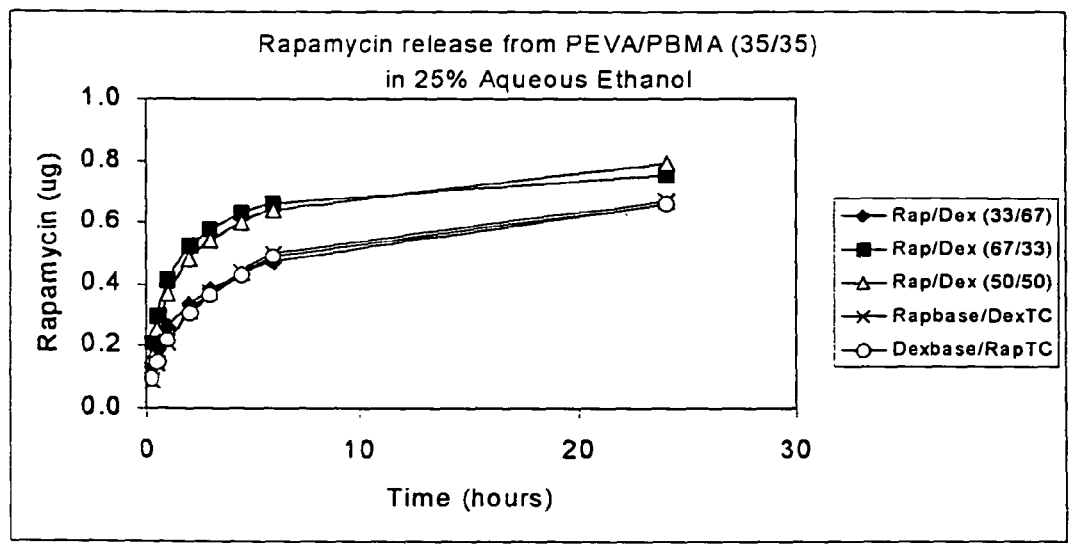
FIGS. 5 and 6 are a graph of the performance characteristics of stents coated according to this invention.

The results from testing the coated stents described above are shown in FIG. 5.

Example 10

This example describes the method for analyzing the release medium for dexamethasone.

The HPLC system used to analyze the samples was a Shimadzu Class-VP Chromatography Laboratory System. This system is equipped with a photodiode array detector. 20 µL of each sample was withdrawn and analyzed on a $C_{18}$-reverse phase column (Waters Symmetry™ Column: 4.6 mm×100 mm $RP_{18}$ 3.5µ). An isocratic mobile phase consisting of methanol/water (55:45 v/v) delivered at a flow rate of 0.8 mL/min. was used for the first 6.5 mins of analysis followed by 100% methanol for 2 minutes; the latter was to ensure removal of rapamycin which is retained on the column. The column was maintained at 25° C. throughout the analysis. Under these analytical conditions dexamethasone had a retention time of 5.9±0.1 minutes. The concentration was determined from a standard curve of concentration versus response (area-under the curve) generated from dexamethasone standards in the range of from 40 ng/mL to 4.0 µg/mL.

Figure 6:
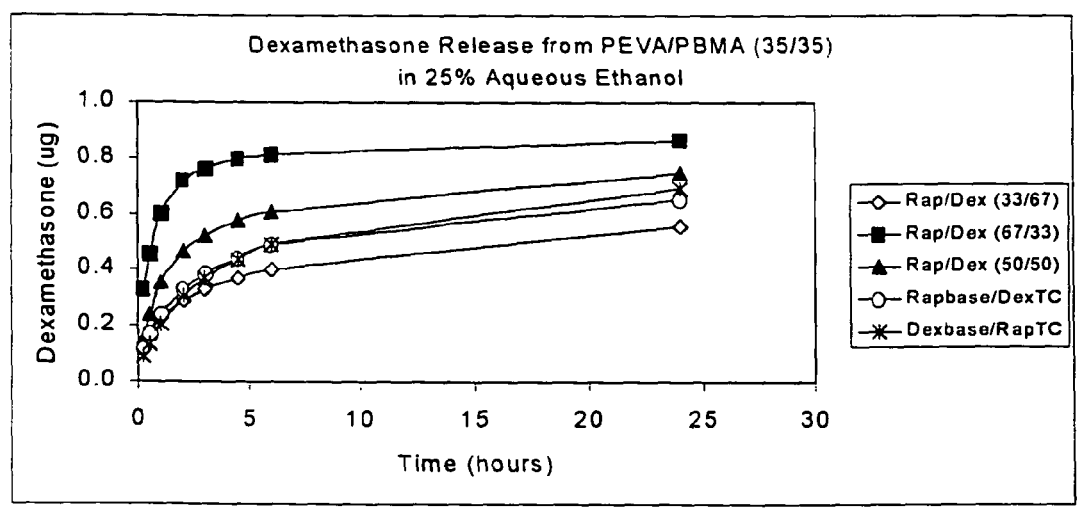
Figure 7:
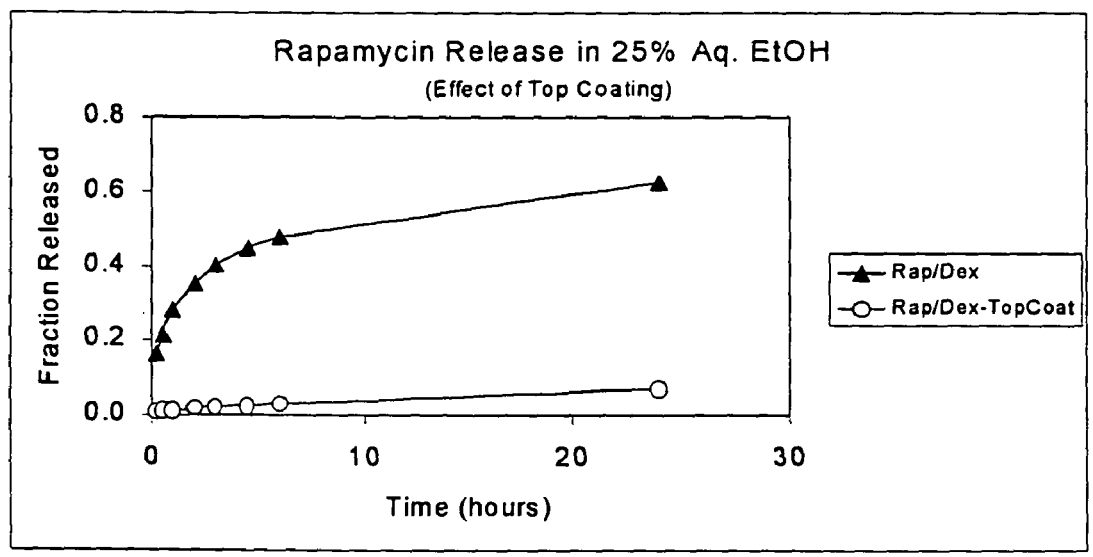
FIGS. 7, 8 and 9 are additional release diagrams displaying results of various tests performed on stents made in accordance with the disclosure.
Figure 8:
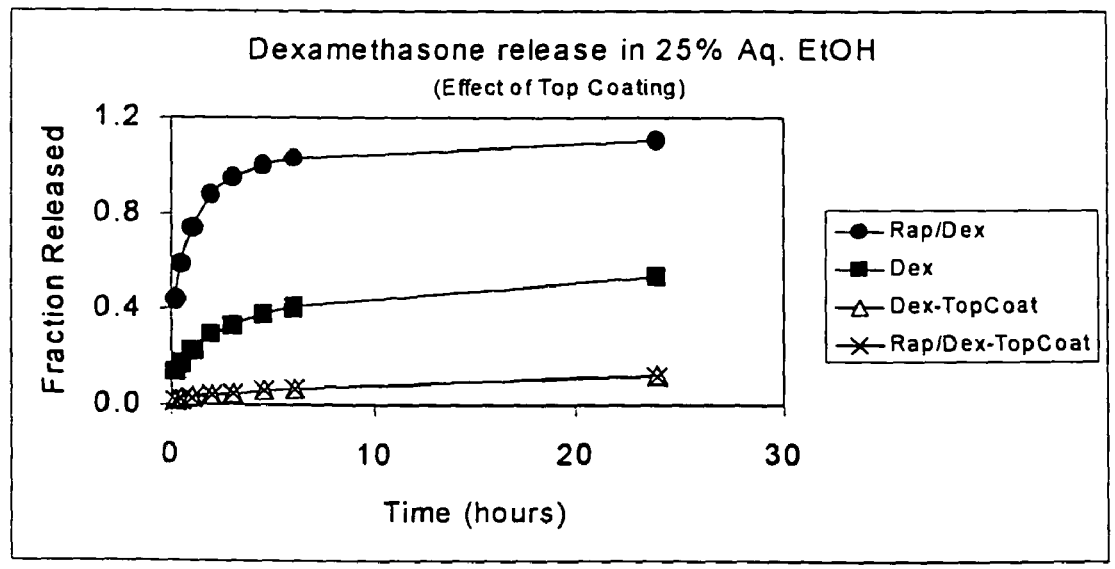
Figure 9:
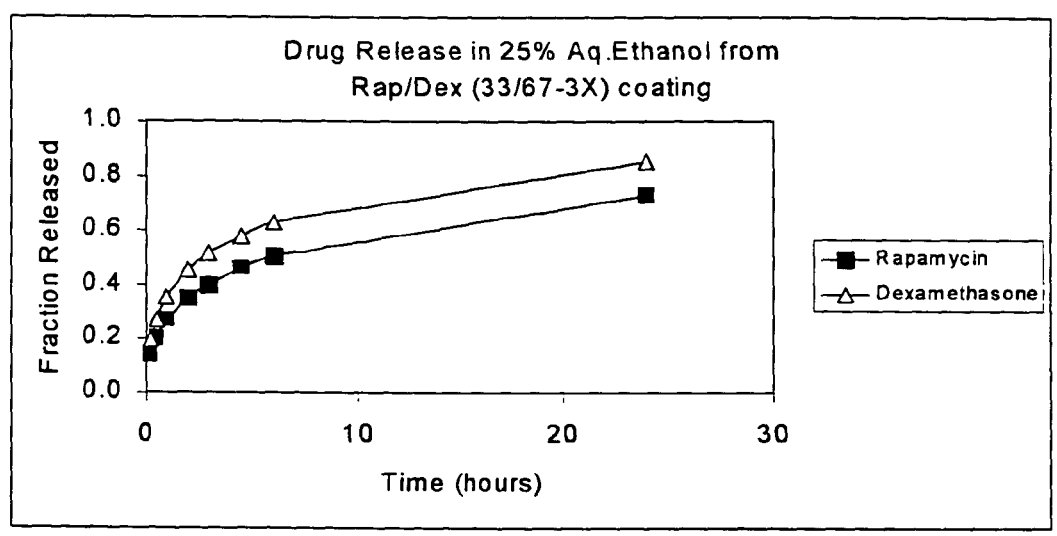

The results from testing the coated stents described above are shown in FIG. 6.

These and other concepts will are disclosed herein. It would be apparent to the reader that modifications are possible to the stent or the drug dosage applied. In any event, however, the any obvious modifications should be perceived to fall within the scope of the invention, which is to be realized from the attached claims and their equivalents.

What is claimed is:

1. A method for treating restenosis comprising an intravascular infusion or delivery by release from a surface of a stent of a combination of at least two agents, including an antiproliferative agent for inhibiting smooth muscle cell growth comprising rapamycin or an analogue thereof and an anti-inflammatory agent for inhibiting smooth muscle growth, both said agents contained in therapeutic dosage amounts.

2. The method of claim 1 wherein the combination of at least two agents further includes a tyrosine kinase inhibitor.

3. The method of claim 1 wherein the anti-inflammatory agent comprises dexamethasone.

4. The method of claim 1 wherein the combination of at least two agents further includes a growth factor or cytokine signal transduction inhibitor.

5. The method of claim 1 wherein the combination of at least two agents further includes an inhibitor of extracellular matrix synthesis.

6. The method of claim 5 wherein the inhibitor of extracellular matrix synthesis comprises halofuginone and the antiproliferative agent is taken from a group consisting of rapamycin, taxol, or vincristine.

* * * * *